United States Patent
Studer et al.

(10) Patent No.: US 6,794,532 B2
(45) Date of Patent: Sep. 21, 2004

(54) HYDROGENATION OF PROCHIRAL KETONES

(75) Inventors: Martin Studer, Basel (CH); Stephan Burkhardt, Gelterkinden (CH); Andreas Pfaltz, Binningen (CH); Christian Exner, Neustadt-Haardt (DE)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 10/411,209

(22) Filed: Apr. 11, 2003

(65) Prior Publication Data

US 2003/0204112 A1 Oct. 30, 2003

(30) Foreign Application Priority Data

Apr. 16, 2002 (CH) .............................................. 0635/02

(51) Int. Cl.[7] .......................... C07C 69/76; C07C 69/66
(52) U.S. Cl. ......................................... 560/60; 560/179
(58) Field of Search ................................... 560/60, 179

(56) References Cited

PUBLICATIONS

Hans–Ulrich Blaser et al., "Enantioselective hydrogenation of α–ketoesters using cinchona modified platinum catalysts and related systems: A review", Catalysis Today 37 (1997) 441–463.

Béla Török et al., New synthesis of a useful C3 chiral building block by a heterogeneous method: enantioselective hydrogenation of pyruvaldehyde dimethyl acetal over cinchona modified Pt/Al$_2$O$_3$ catalysts, Chem. Commun., 1999, 1725–1726.

Martin Studer et al., "Enantioselective hydrogenation of α–keto acetals with cinchona modified Pt catalyst", Chem. Commun., 1999, 1727–1728.

H.U. Blaser et al., "Heterogeneous Enantioselective Hydrogenation of Ethyl Pyruvate Catalyzed by Cinchona–Modified Pt Catalysts: Effect of Modifier Structure", J. Am. Chem. Soc. 2000, 122, 12675–12682.

C. Drzewiczak et al., "Correlation Between Structure and Basicity of Cinchona Alkaloids and Their Derivatives", Polish J. Che., 67, 48ff (1993).

*Primary Examiner*—Johann Richter
*Assistant Examiner*—Paul A. Zucker
(74) *Attorney, Agent, or Firm*—Wenderoth, Lind & Ponack, L.L.P.

(57) ABSTRACT

Process for enantioselectively hydrogenating prochiral ketones to (S)-alcohols using platinum catalysts in the presence of cinchonines or quinidines as modifiers and in the presence of hydrogen, which is characterized in that the modifiers used are cinchonines unsubstituted in the 3-position, 3-ethylidenyl- or 9-methoxycinchonines or derivatives thereof in which the quinoline ring is replaced by other rings.

14 Claims, No Drawings

HYDROGENATION OF PROCHIRAL KETONES

The present invention relates to a process for enantioselectively hydrogenating prochiral ketones to (S)-alcohols using platinum catalysts in the presence of cinchonines or quinidines as modifiers and of hydrogen, which is characterized in that the modifiers used are cinchonines unsubstituted in the 3-position, 3-ethylidenyl- or 9-methoxycinchonines or derivatives thereof in which the quinoline ring is replaced by other rings.

The enantioselective hydrogenation of α-ketoesters using platinum catalysts in the presence of cinchonidine or cinchonine and derivatives of these quinuclidines has been described by H.-U. Blaser et al. in Catalysis Today 37 (1997), pages 441 to 463. This publication also discloses that the enantioselectivity in the presence of cinchonidine for preparing (R)-alcohols is considerably higher than in the presence of cinchonine for preparing (S)-alcohols. The same observation is made by B. Török et al. in Chem. Comm. (1999), pages 1725 to 1726 in the enantioselective hydrogenation of an α-ketodiacetal. The hydrogenation of α-ketoacetals is also described by M. Studer et al. in Chem. Comm. (1999), pages 1727 to 1728. In J. Am. Chem. Soc. (2000) 122, pages 12675 to 12682, H. U. Blaser describes the influence of modification of cinchona alkaloids on the hydrogenation of ethyl pyruvate using cinchona-modified platinum catalysts. It is established that the substitution in the 3-position of the quinuclidine radical has virtually no or only a small influence. In connection with the determination of the $pK_a$ values of cinchona alkaloids, C. Drzewiczak et al. in Polish J. Che., 67, 48ff (1993) mention 3-ethylidenecinchonine without specifying a synthesis or use.

It has now been found that, surprisingly, it is possible to achieve a distinctly higher catalyst activity and increased enantioselectivity in the hydrogenation of prochiral ketones to (S)-alcohols using hydrogen when platinum catalysts are modified with 3-ethylidene- or 9-methoxycinchonines or derivatives thereof in which the quinoline ring is replaced by other rings. The optical yields of (S)-alcohols may be over 90% ee and such high yields could hitherto be achieved in the preparation of (S)-alcohols by this hydrogenation route only by the use of ultrasound (B. Török et al., Ultrasonics Sonochemistry 7 (2000) 151) or by continuously adding modifier (C. LeBlond et al., JACS 121 (1999) 4920).

The invention provides a process for enantioselectively hydrogenating prochiral ketones to (S)-alcohols using platinum catalysts in the presence of cinchonines or quinidines as modifiers and in the presence of hydrogen, which is characterized in that the modifiers used are cinchonines from the group of cinchonines unsubstituted in the 3-position, 3-ethylidenyl- or 9-methoxycinchonines or derivatives thereof in which the quinoline ring is replaced by other rings.

Prochiral ketones are well known. The prochiral α-ketones may be saturated or unsaturated, open-chain or cyclic compounds which preferably have 5 to 30, more preferably 5 to 20, carbon atoms which are unsubstituted or substituted with radicals which are stable under the hydrogenation conditions. The carbon chain may be interrupted by heteroatoms, preferably from the group of —O—, =N— and —NR'—, where R' is H, $C_1$–$C_8$-alkyl, preferably $C_1$–$C_4$-alkyl, $C_5$–$C_8$-cycloalkyl, for example cyclopentyl, cyclohexyl or cyclooctyl, $C_6$–$C_{10}$-aryl, for example phenyl or naphthyl, or $C_7$–$C_{12}$-aralkyl, for example phenylmethyl or phenylethyl. The prochiral ketones preferably have an activating group in the α-position, for example a carboxyl, carboxylic ester, acetal, keto or ether group.

The prochiral ketones may be α-ketocarboxylic acids, α-ketocarboxylic esters, α-ketoethers, α-ketoacetals and α,β-diketones. These prochiral ketones may correspond to the formulae I, II, III, IV and V

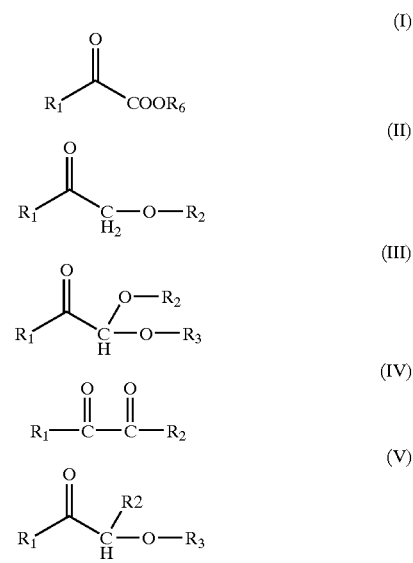

where
$R_1$, $R_2$, $R_3$ and $R_6$ are each independently a monovalent, saturated or unsaturated aliphatic radical having 1 to 12 carbon atoms, a saturated or unsaturated cycloaliphatic radical having 3 to 8 carbon atoms, a saturated or unsaturated heterocycloaliphatic radical having 3 to 8 ring members and one or two heteroatoms from the group of O, N and NR', a saturated or unsaturated cycloaliphatic-aliphatic radical having 4 to 12 carbon atoms, a saturated or unsaturated heterocycloaliphatic-aliphatic radical having 3 to 12 carbon atoms and one or two heteroatoms from the group of O, N and NR', an aromatic radical having 6 to 10 carbon atoms, a heteroaromatic radical having 4 to 9 carbon atoms and one or two heteroatoms from the group of O and N, an aromatic-aliphatic radical having 7 to 12 carbon atoms or a heteroaromatic-aliphatic radical having 5 to 11 carbon atoms and one or two heteroatoms from the group of O and N where R' is H, $C_1$–$C_8$-alkyl, preferably $C_1$–$C_4$-alkyl, $C_5$- or $C_6$-cycloalkyl, $C_6$–$C_{10}$-aryl, for example phenyl or naphthyl, $C_7$–$C_{12}$-aryl, for example phenylmethyl or phenylethyl, $R_1$ and $R_2$ or $R_1$ and $R_6$ together are $C_1$–$C_6$-alkylene or $C_3$–$C_8$-1,2-cycloalkylene, or $C_2$–$C_4$-alkylene or $C_3$–$C_8$-cycloalkylene fused to 1,2-phenylene, and $R_3$ is as defined above, $R_2$ and $R_3$ together are $C_1$–$C_6$-alkylene, $C_1$–$C_8$-alkylidene, $C_3$–$C_8$-1,2-cycloalkylene, $C_3$–$C_8$-cycloalkylidene, benzylidene, 1,2-phenylene, 1,2-pyridinylene, 1,2-naphthylene, or $C_3$–$C_4$-alkylene or $C_3$–$C_8$-1,2-cycloalkylene fused to 1,2-cycloalkylene or 1,2-phenylene, and $R_1$ is as defined above, and $R_1$, $R_2$, $R_3$ and $R_6$ are each unsubstituted or substituted by one or more, identical or different radicals selected from the group of $C_1$–$C_4$-alkyl, $C_2$–$C_4$-alkenyl, $C_1$–$C_4$-alkoxy, $C_1$–$C_4$-haloalkyl, $C_1$–$C_4$-hydroxyalkyl, $C_1$–$C_4$-alkoxymethyl or -ethyl, $C_1$–$C_4$- haloalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$—NHR$_4$, —CO$_2$—NR$_4$R$_5$ where R$_4$ and R$_5$ are each independently C$_1$–C$_4$-alkyl, cyclohexyl, cyclohexylmethyl, phenyl or benzyl.

The heterocyclic radicals are bonded via a ring carbon atom to the oxygen atoms or the carbon atom of the carbonyl groups in the compounds of the formulae I, II, III, IV and V.

Preferred substituents are methyl, ethyl, n- and i-propyl, n- and t-butyl, vinyl, allyl, methyloxy, ethyloxy, n- and i-propyloxy, n- and t-butyloxy, trifluoromethyl, trichloromethyl, β-hydroxyethyl, methoxy- or ethoxymethyl or -ethyl, trifluoromethoxy, cyclohexyl, cyclohexyloxy, cyclohexylmethyl, cyclohexylmethyloxy, phenyl, phenyloxy, benzyl, benzyloxy, phenylethyloxy, phenylethyl, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$—NHR$_4$, —CO$_2$—NR$_4$R$_5$ where R$_4$ and R$_5$ are each independently C$_1$–C$_4$-alkyl, cyclohexyl, cyclohexylmethyl, phenyl or benzyl.

The aliphatic radical is preferably alkyl which may be linear or branched and preferably has 1 to 8, more preferably 1 to 4, carbon atoms, or preferably alkenyl or alkynyl, each of which may be linear or branched and preferably have 2 to 8, more preferably 2 to 4, carbon atoms. When R$_2$ and R$_3$ are alkenyl or alkynyl, the unsaturated bond is preferably in the β-position to the oxygen atom. Examples include methyl, ethyl, n- and i-propyl, n-, i- and t-butyl, pentyl, i-pentyl, hexyl, heptyl, octyl, nonyl, decyl, undecyl and dodecyl, vinyl, allyl, ethynyl and propargyl. A preferred group of aliphatic radicals is methyl, ethyl, n- and i-propyl, n-, i- and t-butyl.

The cycloaliphatic radical is preferably cycloalkyl or cycloalkenyl having preferably 3 to 8, more preferably 5 or 6, ring carbon atoms. Some examples are cyclopropyl, cyclobutyl, cyclopentyl, cyclohexyl, cycloheptyl and cyclooctyl, and also cyclopentenyl, cyclohexenyl and cyclohexadienyl. Particular preference is given to cyclopentyl and cyclohexyl.

The heterocycloaliphatic radical is preferably heterocycloalkyl or heterocycloalkenyl having preferably 3 to 6 carbon atoms, 4 to 7 ring members and heteroatoms selected from the group of —O— and —NR'— where R' is H, C$_1$–C$_8$-alkyl, preferably C$_1$–C$_4$-alkyl, C$_5$- or C$_6$-cycloalkyl, C$_6$–C$_{10}$-aryl, for example phenyl or naphthyl, phenyl or phenylethyl. Some examples are pyrrolidinyl, pyrrolinyl, tetrahydrofuranyl, dihydrofuranyl and piperazinyl.

The cycloaliphatic-aliphatic radical is preferably cycloalkyl-alkyl or -alkenyl having preferably 3 to 8, more preferably 5 or 6, ring carbon atoms, and preferably 1 to 4, or 2–4, more preferably 1 or 2, or 2 or 3, carbon atoms in the alkyl group and alkenyl groups respectively. Examples include cyclopentyl- or cyclohexylmethyl or -ethyl and cyclopentyl- or cyclohexylethenyl.

The heterocycloaliphatic-aliphatic radical is preferably heterocycloalkyl-alkyl or -alkenyl having preferably 3 to 6 carbon atoms, 4 to 7 ring members and heteroatoms selected from the group of —O— and —NR'— where R' is H, C$_1$–C$_8$-alkyl, preferably C$_1$–C$_4$-alkyl, C$_5$- or C$_6$-cloalkyl, C$_6$–C$_{10}$-aryl, for example phenyl or naphthyl, phenyl or phenylethyl, and preferably 1 to 4, more preferably 1 or 2, carbon atoms in the alkyl group and 2 to 4, more preferably 2 or 3, carbon atoms in the alkenyl group. Examples include pyrrolidinylmethyl or -ethyl or -ethenyl, pyrrolinylmethyl or -ethyl or -ethenyl, tetrahydrofuranylmethyl or -ethyl or -ethenyl, dihydrofuranylmethyl or -ethyl or -ethenyl, and piperazinylmethyl or -ethyl or -ethenyl.

The aromatic radicals are preferably naphthyl and in particular phenyl.

The aromatic-aliphatic radicals are preferably phenyl- or naphthyl-C$_1$–C$_4$-alkyl or -C$_2$–C$_4$-alkenyl. Some examples are benzyl, naphthylmethyl, β-phenylethyl and β-phenylethenyl.

The heteroaromatic radicals are preferably 5- or 6-membered, optionally fused ring systems. Some examples are pyridinyl, pyrimidinyl, pyrazinyl, pyrrolyl, furanyl, oxazolyl, imidazolyl, benzofuranyl, indolyl, benzimidazolyl, quinolinyl, isoquinolinyl, quinazolinyl, quinoxalinyl.

The heteroaromatic-aliphatic radicals are preferably 5- or 6-membered, optionally fused ring systems which are bonded via one of their carbon atoms to the free bond of an alkyl group or alkenyl group where the alkyl group preferably contains 1 to 4, more preferably 1 or 2, carbon atoms, and the alkenyl group preferably contains 2 to 4, more preferably 2 or 3, carbon atoms. Some examples are pyridinylmethyl or ethyl or -ethenyl, pyrimidinylmethyl or -ethyl or -ethenyl, pyrrolylmethyl or -ethyl or -ethenyl, furanylmethyl or -ethyl or -ethenyl, imidazolylmethyl or -ethyl or -ethenyl, indolylmethyl or -ethyl or -ethenyl.

R$_6$ is preferably an aliphatic, cycloaliphatic or araliphatic radical, and more preferably linear C$_1$–C$_4$-alkyl.

More preferred compounds of the formulae I, II, III, IV and V include those where R$_1$, R$_2$, R$_3$ and R$_6$ are each independently linear or branched C$_1$–C$_8$-alkyl, C$_4$–C$_7$-cycloalkyl or C$_4$–C$_6$-heterocycloalkyl having heteroatoms from the group of O and N, C$_6$–C$_{10}$-aryl or C$_4$–C$_9$-heteroaryl having heteroatoms from the group of O and N, C$_4$–C$_7$-cycloalkyl-C$_1$–C$_4$-alkyl or C$_3$–C$_6$-heterocycloalkyl-C$_1$–C$_4$-alkyl having heteroatoms from the group of O and N, C$_6$–C$_{10}$-aryl-C$_1$–C$_4$-alkyl or C$_4$–C$_9$-heteroaryl-C$_1$–C$_4$-alkyl having heteroatoms from the group of O and N, R$_1$ and R$_2$ or R$_1$ and R$_6$ together are C$_1$–C$_4$-alkylene or C$_4$–C$_7$-1,2-cycloalkylene, or C$_2$–C$_4$-alkylene or C$_4$–C$_7$-cycloalkylene fused to 1,2-phenylene, and R$_3$ is as defined above, R$_2$ and R$_3$ together are C$_1$–C$_4$-alkylene, C$_1$–C$_4$-alkylidene, C$_4$–C$_7$-1,2-cycloalkylene, C$_4$–C$_7$-cycloalkylidene, benzylidene, 1,2-phenylene, 1,2-pyridinylene, 1,2-naphthylene, or C$_3$–C$_4$-alkylene or C$_4$–C$_7$-cloalkylene fused to 1,2-cycloalkylene or 1,2-phenylene, and R$_1$ is as defined above where R$_1$, R$_2$, R$_3$ and R$_6$ are each unsubstituted or substituted by one or more, identical or different radicals selected from the group of C$_1$–C$_4$-alkyl, C$_1$–C$_4$-alkoxy, C$_1$–C$_4$-haloalkyl, C$_1$–C$_4$-hydroxyalkyl, C$_1$–C$_4$-alkoxymethyl or -ethyl, C$_1$–C$_4$-haloalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —OR$_4$, —OC(O)R$_4$, —NH$_2$, —NHR$_4$, —NR$_4$R$_5$, —NH—C(O)—R$_4$, —NR$_4$—C(O)R$_4$, —CO$_2$R$_4$, —CO$_2$—NH$_2$, —CO$_2$—NHR$_4$, —CO$_2$—NR$_4$R$_5$ where R$_4$ and R$_5$ are each independently C$_1$–C$_4$-alkyl, cyclohexyl, phenyl or benzyl.

A preferred subgroup of the compounds of the formulae I, II, III, IV and V are those where R$_1$, R$_2$, R$_3$ and R$_6$ are each independently linear or branched C$_1$–C$_4$-alkyl, C$_2$–C$_4$-alkenyl, C$_5$–C$_6$-cycloalkyl, phenyl, phenylethenyl, $C_5$–$C_6$-cycloalkyl-$C_1$–$C_2$-alkyl, or $C_6$–$C_{10}$-aryl-$C_1$–$C_2$-alkyl, $R_1$ and $R_2$ or $R_1$ and $R_6$ together are $C_1$–$C_3$-alkylene or $C_5$–$C_6$-1,2-cycloalkylene, $R_2$ and $R_3$ together are $C_2$–$C_4$-alkylene, $C_1$–$C_4$-alkylidene, $C_5$–$C_6$-1,2-cycloalkylene, $C_5$–$C_6$-cycloalkylidene, benzylidene, 1,2-phenylene where $R_1$, $R_2$, $R_3$ and $R_6$ are each unsubstituted or substituted as defined previously.

A particularly preferred subgroup of the compounds of the formulae I, II, III, IV and V are those where $R_1$ and $R_6$ are each $C_1$–$C_4$-alkyl, $C_2$–$C_4$-alkenyl, cyclohexyl, phenyl, benzyl, phenylethyl or phenylethenyl, $R_2$ and $R_3$ are each independently linear or branched $C_1$–$C_4$-alkyl, cyclohexyl, phenyl, benzyl or phenylethyl, $R_1$ and $R_2$ or $R_1$ and $R_6$ together are $C_2$–$C_3$-alkylene or 1,2-cyclohexylene, $R_2$ and $R_3$ together are $C_2$–$C_3$-alkylene, $C_1$–$C_4$-alkylidene, 1,2-cyclohexylene, cyclohexylidene, benzylidene or 1,2-phenylene where $R_1$, $R_2$, $R_3$ and $R_6$ are each unsubstituted or substituted by methyl, ethyl, n- and i-propyl, n- and t-butyl, vinyl, allyl, methyloxy, ethyloxy, n- and i-propyloxy, n- and t-butyloxy, trifluoromethyl, trichloromethyl, β-hydroxyethyl, methoxy- or ethoxymethyl or -ethyl, trifluoromethoxy, cyclohexyl, cyclohexyloxy, cyclohexylmethyl, cyclohexylmethyloxy, phenyl, phenyloxy, benzyl, benzyloxy, phenylethyloxy, phenylethyl, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$—NH$_4$, —CO$_2$—NR$_4$R$_5$ where $R_4$ and $R_5$ are each independently $C_1$–$C_4$-alkyl, cyclohexyl, cyclohexylmethyl, phenyl or benzyl.

Some of the compounds of the formulae I, II, III, IV and V are known or can be prepared in a manner known per se by means of similar processes.

The compounds of the formulae I, II, III, IV and V are hydrogenated to chiral secondary alcohols of the formulae VI, VII, VIII and IX

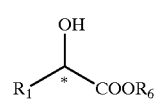

(VI)

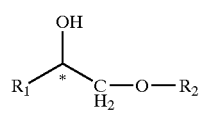

(VII)

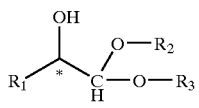

(VIII)

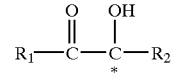

(IX)

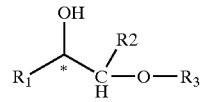

(X)

where $R_1$, $R_2$, $R_3$ and $R_6$ are each as previously defined and the symbol * represents predominantly the S-form of one of the stereoisomers.

Platinum catalysts are known, extensively described and commercially available. It is possible to use either platinum in metal form, for example as a powder, or, which is preferred, platinum metal applied to finely divided supports. Examples of suitable supports include carbon, metal oxides, for example SiO$_2$, TiO$_2$, Al$_2$O$_3$, metal salts, and natural or synthetic silicates. The catalyst may also be a platinum colloid. The amount of platinum metal on the support may be, for example, 1 to 10% by weight, preferably 3 to 8% by weight, based on the support. Before their use, the catalysts may be activated by treating with hydrogen at elevated temperature and/or with ultrasound. Preferred catalysts are platinum on Al$_2$O$_3$.

The cinchonines unsubstituted in the 3-position, 3-ethylidenyl- or 9-methoxycinchonines or derivatives thereof to be used according to the invention may, for example, correspond to the formula XI with 8(R),9(S)-configuration

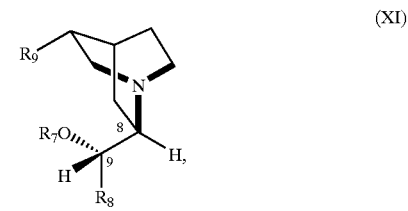

(XI)

where $R_9$ is CH$_2$=CH— or CH$_3$CH$_2$— and $R_7$ is methyl, or $R_9$ is H or CH$_3$—CH= and $R_7$ is H or methyl, and $R_8$ is unsubstituted or $C_1$–$C_4$-alkyl- or $C_1$–$C_4$-alkoxy-substituted $C_6$–$C_{14}$-aryl or $C_5$–$C_{13}$-heteroaryl having heteroatoms selected from the group of —N=, —O—, —S— and —N($C_1$–$C_4$-alkyl)-.

$R_8$ as aryl and heteroaryl may be a monocyclic or fused polycyclic radical having preferably 2 or three rings. The rings preferably contain 5 or 6 ring members. Some examples are phenyl, furyl, thiophenyl, N-methylpyrrolyl, pyridinyl, naphthyl, tetrahydronaphthyl, anthracenyl, phenanthryl, quinolinyl, tetrahydroquinolinyl, isoquinolinyl, indenyl, fluorenyl, benzofuranyl, dihydrobenzofuranyl, benzothiophenyl, dihydrobenzothiophenyl, N-methylindolyl, dihydro-N-methylindolyl, dibenzofuranyl, dibenzothiophenyl and N-methylcarbazolyl.

The cinchonines unsubstituted in the 3-position, 3-ethylidenyl- or 9-methoxycinchonines or derivatives thereof to be used according to the invention preferably correspond to the formula XIa with 8(R),9(S)-configuration

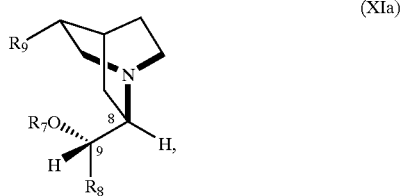

(XIa)

where
R$_9$ is CH$_2$=CH— or CH$_3$CH$_2$— and R$_7$ is methyl, or
R$_9$ is H or CH$_3$—CH= and R$_7$ is H or methyl,
R$_8$ is a radical of the formulae

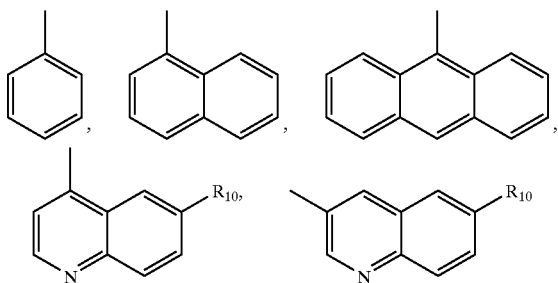

and R$_{10}$ is H, OH or C$_1$-C$_4$-alkoxy.

R$_{10}$ is preferably H, OH or methoxy.

The compounds of the formula XI where R$_9$ is CH$_2$=CH— or CH$_3$CH$_2$— and R$_7$ is methyl may be prepared in a simple manner by methylating the hydroxyl group bonded to C9 of appropriate natural cinchona alkaloids. Compounds where R$_9$ is ethyl are obtainable by hydrogenating the R$_9$ vinyl group.

The compounds of the formula XI where R$_9$ is CH$_3$—CH= may be prepared by isomerizing the R$_9$ vinyl group in the presence of metal complexes, for example ruthenium/phosphine complexes. An implementation of the process is described in the examples. In general, mixtures of the Z- and E-isomers are obtained which can be used directly as such.

The compounds of the formula XI which are not derived from natural cinchonines are synthetically accessible, for example, by means of reacting quinuclidine N-oxide with lithium alkyls (Li-methyl or Li-n-butyl) with aldehydes R$_8$—CH=O, subsequent reaction with a Lewis acid, for example TiCl$_3$, and ensuing alkaline hydrolysis. The diastereomers may be separated chromatographically on silica gel, and the enantiomers may be separated chromatographically on chiral columns. This is described in more detail in the examples.

The platinum metal may be used, for example, in an amount of 0.01 to 10% by weight, preferably 0.05 to 10% by weight and more preferably 0.1 to 5% by weight, based on the prochiral ketone used, although amounts of 0.1 to 3% by weight, or 0.1 to 1% by weight generally suffice. The increased activity of the hydrogenation system to be used according to the invention allows smaller total amounts of catalyst, which makes the process more economic.

The modifier may be used, for example, in an amount of 0.1 to 10 000% by weight, preferably 1 to 500% by weight and more preferably 10 to 200% by weight, based on the platinum metal used. The modifier may be introduced into the reaction vessel together with the platinum metal catalyst, or the platinum metal catalyst may be impregnated beforehand with the modifier.

The hydrogenation is preferably carried out under a hydrogen pressure of up 200 bar, more preferably up to 150 bar and particularly preferably 10 to 100 bar.

The reaction temperature may be, for example, −50 to 100° C., more preferably 0 to 50° C. and particularly preferably 0 to 35° C. It is generally possible to achieve better enantioselectivies at low temperatures.

The reaction may be carried out without or in an inert solvent or mixtures of solvents. Examples of suitable solvents include aliphatic, cycloaliphatic and aromatic hydrocarbons (pentane, hexane, petroleum ether, cyclohexane, methylcyclohexane, benzene, toluene, xylene), ethers (diethyl ether, dibutyl ether, ethylene glycol dimethyl ether, ethylene glycol diethyl ether, diethylene glycol dimethyl ether, tetrahydrofuran, dioxane), water, alcohols (methanol, ethanol, propanol, butanol, ethylene glycol, diethylene glycol, ethylene glycol monomethyl or monoethyl ether, diethylene glycol monomethyl or monoethyl ether), ketones (acetone, methyl isobutyl ketone), carboxylic esters and lactones (ethyl or methyl acetate, valerolactone), N-substituted carboxamides and lactams (dimethylformamide, N-methylpyrrolidone), and carboxylic acids (acetic acid, propionic acid, butyric acid). The choice of the solvent may be used to influence the optical yield. For example, aromatic hydrocarbons (benzene, toluene, xylene) have proven particularly useful in the case of α-ketoacetals and aromatic α-ketocarboxylic esters, while better results can be achieved using carboxylic acids, for example acetic acid, in the case of aliphatic α-ketocarboxylic acids.

The process according to the invention may, for example, be carried out in such a way that the catalyst is initially charged in an autoclave with the nitrogen base, optionally with a solvent, then the prochiral α-ketone is added, then the air is displaced with an inert gas, for example noble gases, hydrogen is injected in and then the reaction is started, optionally with stirring or shaking, and hydrogenation is effected until no more hydrogen takeup is observed. The α-hydroxyl compound formed may be isolated and purified by customary methods, for example distillation, crystallization and chromatographic methods.

The invention also provides compounds of the formula XIb

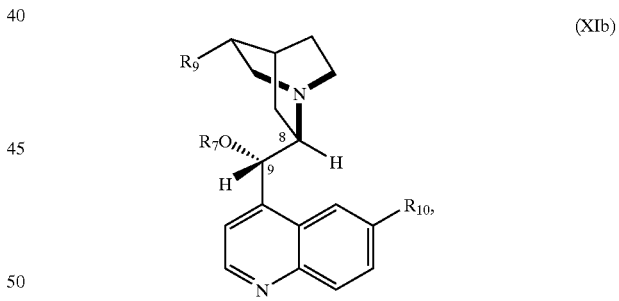

(XIb)

where
R$_9$ is CH$_2$=CH— or CH$_3$CH$_2$— and R$_7$ is methyl, or
R$_9$ is H or CH$_3$—CH= and R$_7$ is H or methyl, and
R$_{10}$ is H or C$_1$-C$_4$-alkoxy.

When R$_7$ is H, R$_{10}$=H and R$_9$ is CH$_2$=CH—, the molecule is cinchonine (Cn) and when R$_7$ is H, R$_{10}$=H and R$_9$ is CH$_3$CH$_2$—, the molecule is hydrocinchonine (HCn).

The (S)-α-alcohols which can be prepared according to the invention are valuable intermediates for the preparation of natural active ingredients (B. T. Cho et al. in Tetrahedron: Asymmetry Vol. 5, No. 7 (1994), pages 1147 to 1150), and synthetic active pharmaceutical ingredients and pesticides. The (S)-α-alcohols obtainable may be converted beforehand by known processes to derivatives which may then be used as intermediates for the preparation of active ingredients.

The acid hydrolysis of, for example, α-ketoacetals leads to 1,4-dioxanes or the corresponding aldehydes which are either hydrogenated to 1,2-diols having a secondary optically active hydroxyl group, or reacted with amines in the presence of phenylboric acids to optionally substituted optically active 1-phenyl-1-amino-2-hydroxyalkanes. After the protection of the OH group, for example by reaction with benzyl bromide, the hydroxyl-protected aldehydes may be obtained by reacting with strong acids and may be hydrogenated to 1,2-diols or converted to S-α-hydroxycarboxylic acids by oxidation (for example with chromium trioxide) and removing the protecting group.

The examples which follow illustrate the invention in detail. The optical yield is determined by gas chromatography using a Supelco Beta-dex column (article No. 2-4301), hydrogen as the carrier gas and elevated temperatures; or by means of HPLC (Chiracel OD column, using 95:5 hexane/isopropanol). The conversion is determined by means of $^1$H NMR.

A) Preparation of Modifiers

EXAMPLE A1

Preparation of O-Methylcinchonine (MeO-Cn, $R_7$ in Formula XIb=Methyl, $R_{10}$=H, $R_9$=CH$_2$=CH—)

0.60 g of potassium hydride (15.0 mmol) is weighed into a 250 ml two-necked flask equipped with a reflux condenser and dropping funnel under argon. This is washed three times with absolute n-pentane and subsequently suspended in 50 ml of absolute tetrahydrofuran. 3.24 g (11.0 mmol) of cinchonine (Cn) are then added in portions with ice cooling, and obvious gas development can be observed. After completion of addition, stirring is continued at 0° C. for about another half hour until an almost clear orange solution is obtained. The solution is then heated to 50° C. for a further 2 hours until no more gas development can be detected. At room temperature (RT), 0.69 ml (1.56 g; 11.0 mmol) of iodomethane are then slowly added dropwise. The solution is stirred at RT for 12 hours and then hydrolyzed using 50 ml of H$_2$O with ice cooling. The organic and the aqueous phases are separated, and the aqueous phase is extracted three times more with ethyl acetate (EA). The combined organic phases are dried over MgSO$_4$ and concentrated on a rotary evaporator (RE). Chromatographic purification on a silica gel column (EA/Nethyl$_3$ 9:1) and drying under high vacuum give 2.82 g (83%) of the title compound as a pale yellow solid. Recrystallization from a little n-hexane provides 2.50 g (74%) of colourless, rhombic crystals. Melting point: 113–114° C.; $[\alpha]_D^{20}$: +242° (c=0.90, CHCl$_3$).

EXAMPLE A2

Preparation of O-Methylquinidine (MeO-Qd, $R_7$ in Formula XIb=Methyl, $R_{10}$=Omethyl, $R_9$=CH$_2$=CH—)

The procedure of Example A1 is followed using quinidine. The title compound is obtained in a yield of 71% as a yellow, viscous oil. $[\alpha]_D^{20}$: +202° (c=0.78, CHCl$_3$).

EXAMPLE A3

Preparation of (E)/(Z)-Isocinchonine (iso-Cn, $R_7$ in Formula XIb=H, $R_{10}$=H, $R_9$=CH$_3$—CH=)

In a 100 ml two-necked flask equipped with a reflux condenser, 106.0 mg (408 μmol) of triphenylphosphine and 25.0 mg (100 μmol) of RuCl$_3$.nH$_2$O in 30 ml absolute dimethylformamide under argon are heated to 150° C. until a dear orange solution is formed (approx. 15 minutes). The solution is subsequently allowed to cool to 100° C., then 2 g (6.8 mmol) of cinchonine are added and the solution is heated once again to 150° C. for half an hour. The still-hot reaction mixture is poured into 100 ml of precooled water and stirred at 5° C. for 1 hour. The precipitated colourless solid is filtered off and dried under high vacuum. After recrystallization from dimethoxyethane, 1.10 g (55%) of the title compound as an inseparable 1:1 mixture of the Z- and E-isomers are obtained in the form of fine, colourless needles. Melting point of the diastereomer mixture: 229–231° C.; $[\alpha]_D^{20}$: +173° (c=0.93, CHCl$_3$).

EXAMPLE A4

Preparation of (E)/(Z)-Apoisoquinidine (iso-Qd, $R_7$ in the Formula XIb=H, $R_{10}$=Omethyl, $R_9$=CH$_3$—CH=)

The procedure of Example A3 is followed using quinidine. For isolation, the reaction mixture after aqueous workup is initially adjusted to a pH of 9–10 using 1 M NaOH solution and then extracted repeatedly with methylene chloride. The combined organic phases are concentrated under high vacuum and then the residue is recrystallized from diethyl ether. The title compound is obtained as an inseparable 1:1 mixture of the Z- and E-isomers in the form of a beige solid. Melting point of the diastereomer mixture: 161–165° C.; $[\alpha]_D^{20}$: +148° (c=0.88, CHCl$_3$).

EXAMPLE A5

Preparation of Rubanol, $R_7$ in Formula XIa=H, $R_9$=H, $R_8$=Naphthyl

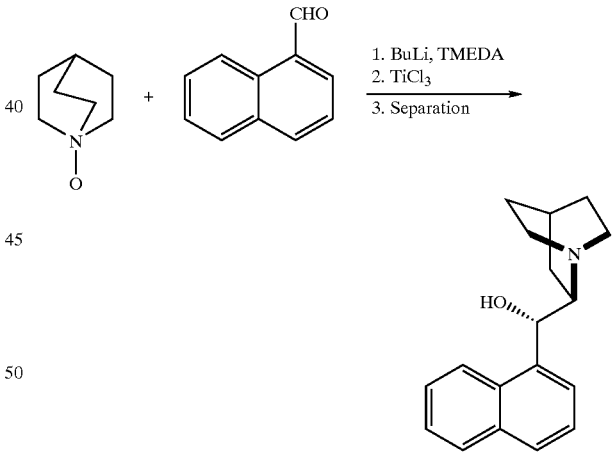

BuLi: n-butyllithium; TMEDA: tetramethylethylenediamine.

3.58 ml (5.7 mmol) of n-butyllithium (1.6 M in n-hexane) are added dropwise at −78° C. within 30 min to a solution of 0.66 g (5.2 mmol) of azabicyclo[2.2.2]octane N-oxide and 0.86 ml (0.67 g; 5.7 mmol) of TMEDA in 30 ml of absolute THF. The yellow reaction solution is stirred at −78° C. for 1 h. 0.78 g (5.0 mmol) of α-naphthaldehyde in 10 ml of absolute tetrahydrofuran is then added slowly. Stirring is continued at −78° C. for 2 h and the mixture is then subsequently heated within 12 h to room temperature (RT). After adding 10 ml of saturated, aqueous NH$_4$Cl solution, the mixture is stirred at RT for 30 minutes.

The reduction of the N-oxide to the tertiary amine is carried out in situ using TiCl$_3$ solution (1.9 M in 2.0 M aqueous HCl) without further workup. Titanium(III) hydrochloric acid solution is added with ice cooling until a deep violet colour remains even after prolonged stirring. After heating to RT, the reaction mixture is set to pH=10 using 15 per cent aqueous NaOH solution. The precipitated salts are filtered through Celite, and the filtrate is repeatedly extracted using ethyl acetate. The combined organic phases are washed with saturated aqueous NaCl solution, dried over potassium carbonate, filtered and concentrated on a rotary evaporator. The $^1$H NMR spectrum of the crude product shows that the two diastereomers are formed in a 1:1 ratio. Chromatographic purification on a silica gel column (ethyl acetate/triethylamine, 9:1) provides 0.55 g (41%) of the desired erythro-isomer as colourless needles. Preparative HPLC (Daicel Chiralcel OD®, 20×250 mm, n-hexane/isopropanol, 95:5, 1% of diethylamine), 20.0 ml/min, t$_r$[(−)-enantiomer]=10.4 min, t$_r$[(+)-enantiomer]=15.9 min) separates the two erythro-enantiomers to 98% ee in each case. $^1$H NMR (CDCl$_3$, 400 MHz): 8.06 (d, 1H, $^3$J=8.2 Hz), 7.86 (dd, 1H, $^3$J=7.8 Hz, $^4$J=1.5 Hz), 7.76 (d, 1H, $^3$J=8.2 Hz), 7.71 (d, 1H, $^3$J=7.1 Hz), 7.48–7.41 (m, 3H), 5.77 (d, 1H, $^3$J=4.6 Hz), 3.58–2.52 (m, 6H), 1.91–1.31 (m, 7H). $^{13}$C NMR (CDCl$_3$, 101 MHz): 139.7 (q), 133.8 (q), 130.5 (q), 128.9 (t), 127.8 (t), 126.0 (t), 125.4 (2x t), 123.4 (t), 123.2 (t), 72.9 (t), 60.1 (t), 50.7 (s), 43.9 (s), 26.6 (s), 26.5 (s), 25.8 (s), 22.1 (t).

Melting point: 202–204° C. $[\alpha]_D^{20}$: −135° (c=0.35, CHCl$_3$).

EXAMPLE A6

Preparation of EXN-1, R$_7$ in Formula XIa=H, R$_9$= H, R$_8$=Quinoline

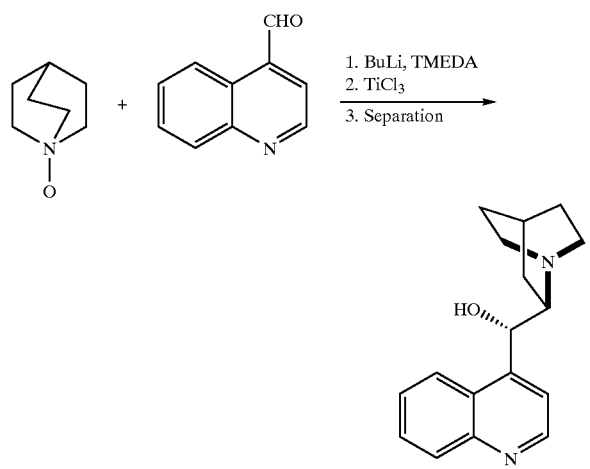

The synthesis is carried out in a similar manner to Example A5 using 3.58 g (28.2 mmol) of azabicyclo[2.2.2]octane N-oxide, 4.70 ml (31.1 mmol) of TMEDA, 20.00 ml (32.0 mmol) of n-butyllithium (1.6 M in n-hexane) and 5.00 g (31.7 mmol) of quinoline-4-carbaldehyde. The $^1$H NMR spectrum of the crude product shows that the two diastereomers are formed in a 1:1 ratio. Chromatographic purification on a silica gel column (ethyl acetate/triethylamine, 9:1) provides 2.95 g (39%) of rubanol as a colourless solid. Semipreparative HPLC (Chiracel OD-H®, n-heptane/isopropanol 98:2, 0.5 ml/min, t$_r$[(−)-rubanol]=52.1 min, t$_r$[(+)-rubanol]=63.8 min) separates the erythro-enantiomers from each other to 99% ee in each case. $^1$H NMR (CDCl$_3$, 400 MHz): 8.90 (d, 1H, $^3$J=4.6 Hz), 8.12 (dd, 1H, $^3$J=8.6 Hz, $^4$J=0.8 Hz), 7.97 (d, 1H, $^3$J=8.4 Hz), 7.69–7.64 (m, 2H), 7.43 (dt, 1H, $^3$J=7.0 Hz, $^4$J=1.2 Hz), 5.78 (d, 1H, $^3$J=3.5 Hz), 4.70 (br, 1H), 3.57–3.52 (m, 1H), 3.14–2.49 (m, 4H), 1.89–1.27 (m, 7H). $^{13}$C NMR (CDCl$_3$, 101 MHz): 150.6 (q), 148.7 (t), 148.4 (q), 130.8 (t), 129.4 (t), 126.9 (t), 126.1 (t), 125.5 (q), 123.4 (t), 118.7 (t), 72.0 (t), 60.4 (t), 51.1 (s), 44.3 (s), 26.7 (s), 26.3 (s), 25.9 (s), 22.3 (t). Melting point: 222–224° C. $[\alpha]_D^{20}$: +99° (c=0.51, CHCl$_3$).

B) Hydrogenations of Prochiral α-Ketones

EXAMPLES B1–B8

Hydrogenation of Methyl Pyruvate [CH$_3$—C(O)—COOC$_2$H$_5$] to Ethyl (2S)-Hydroxypropionate In a 2 ml microanalysis bottle equipped with a magnetic stirrer, 10 mg of 5% Pt/Al$_2$O$_3$ (catalyst JMC 94, batch 14017/01, pretreated under hydrrogen at 400° C. for 2 hours) are initially charged and admixed with 1 mg of modifier. 100 microlitres of ethyl pyruvate dissolved in 1 ml of solvent are then added, and the microanalysis bottle is then placed in a 50 ml pressure autoclave together with three further microanalysis bottles. The autoclave is purged three times with argon and three times with hydrogen and then 60 bar of hydrogen are injected in. The reactions are started by switching on the magnetic stirrer and carried out at room temperature. After 60 to 70 minutes, the pressure is dissipated, and the autoclave is purged three times with argon and opened. The catalysts are filtered off and the reaction mixture is analysed. The results are reported in Table 1.

TABLE 1

[Abbreviations: AcOH is acetic acid]

| Example No. | Modifier | Solvent | ee (%) | Conversion (%) |
|---|---|---|---|---|
| B1 | MeO-Cn | AcOH | 85 | 100 |
| B2 | MeO-Qd | AcOH | 90 | 100 |
| B3 | iso-Cn | AcOH | 88 | 100 |
| B4 | iso-Qd | AcOH | 84 | 100 |
| B5 | EXN-1 | AcOH | 88 | 100 |
| B6 | rubanol | AcOH | 82 | 100 |
| Comparative | Cn | AcOH | 88 | >99 |
| Comparative | HCn | AcOH | 88 | >99 |
| B7 | MeO-Cn | toluene | 31 | 100 |
| B8 | MeO-Qd | toluene | 53 | 100 |
| B9 | iso-Cn | toluene | 74 | 100 |
| B10 | iso-Qd | toluene | 61 | 100 |
| B11 | EXN-1 | toluene | 69 | 100 |
| B12 | rubanol | toluene | 67 | 100 |
| Comparative | Cn | toluene | 68 | >99 |
| Comparative | HCn | toluene | 65 | >99 |

EXAMPLES B13–B24

Hydrogenation of Methyl Phenylketoacetate

The procedure of Example B1 is followed using methyl phenylketoacetate. The results are reported in Table 2.

TABLE 2

| Example No. | Modifier | Solvent | ee (%) | Conversion (%) |
|---|---|---|---|---|
| 13 | MeO-Cn | AcOH | 18 | 100 |
| B14 | MeO-Qd | AcOH | 15 | 100 |
| B15 | iso-Cn | AcOH | 75 | 100 |

TABLE 2-continued

| Example No. | Modifier | Solvent | ee (%) | Conversion (%) |
|---|---|---|---|---|
| B16 | iso-Qd | AcOH | 15 | 100 |
| B17 | EXN-1 | AcOH | 53 | 100 |
| B18 | rubanol | AcOH | 37 | 100 |
| Comparative | HCn | AcOH | 51 | 100 |
| B19 | MeO-Cn | toluene | 31 | 100 |
| B20 | MeO-Qd | toluene | 8 | 100 |
| B21 | iso-Cn | toluene | 80 | 100 |
| B22 | iso-Qd | toluene | 66 | 100 |
| B23 | EXN-1 | toluene | 70 | 100 |
| B24 | rubanol | toluene | 90 | 100 |
| Comparative | HCn | toluene | 78 | 100 |

EXAMPLES B25–B36

Hydrogenation of Methylglyoxal 1,1-dimethyl Acetal

The procedure of Example B1 is followed using methylglyoxal 1,1-dimethyl acetal. The results are reported in Table 3.

TABLE 3

| Example No. | Modifier | Solvent | ee (%) | Conversion (%) |
|---|---|---|---|---|
| B25 | MeO-Cn | AcOH | 93 | 100 |
| B26 | MeO-Qd | AcOH | 92 | 100 |
| B27 | iso-Cn | AcOH | 82 | 97 |
| B28 | iso-Qd | AcOH | 81 | 100 |
| B29 | EXN-1 | AcOH | 84 | 100 |
| B30 | rubanol | AcOH | 69 | 100 |
| Comparative | Cn | AcOH | 76 | 94 |
| Comparative | HCn | AcOH | 78 | 96 |
| B31 | MeO-Cn | toluene | 19 | 71 |
| B32 | MeO-Qd | toluene | 29 | 77 |
| B33 | iso-Cn | toluene | 42 | 79 |
| B34 | iso-Qd | toluene | 26 | 55 |
| B35 | EXN-1 | toluene | 19 | 100 |
| B36 | rubanol | toluene | 72 | 100 |
| Comparative | Cn | toluene | 33 | 55 |
| Comparative | HCn | toluene | 20 | 65 |

EXAMPLES B37–B48

Hydrogenation of Ethyl 2,4-diketobutyrate to Ethyl (S)-4-keto-2-hydroxybutyrate

The procedure of Example B1 is followed using ethyl 2,4-diketobutyrate. The results are reported in Table 4.

TABLE 4

| Example No. | Modifier | Solvent | ee (%) | Conversion (%) |
|---|---|---|---|---|
| B37 | MeO-Cn | AcOH | 59 | 100 |
| B38 | MeO-Qd | AcOH | 73 | 100 |
| B39 | iso-Cn | AcOH | 67 | 100 |
| B40 | iso-Qd | AcOH | 60 | 100 |
| B41 | EXN-1 | AcOH | 74 | 98 |
| B42 | rubanol | AcOH | 61 | 96 |
| Comparative | HCn | AcOH | 64 | 100 |
| B43 | MeO-Cn | toluene | 43 | 100 |
| B44 | MeO-Qd | toluene | 31 | 90 |
| B45 | iso-Cn | toluene | 70 | 100 |
| B48 | iso-Qd | toluene | 66 | 93 |
| B47 | EXN-1 | toluene | 66 | 100 |
| B48 | rubanol | toluene | 35 | 100 |
| Comparative | HCn | toluene | 64 | 100 |

EXAMPLES B49–B60

Hydrogenation of Ethyl 2,4-dioxo-4-phenylbutyrate to Ethyl (S)-4-keto-4-phenyl-2-hydroxybutyrate The procedure of Example B1 is followed using ethyl 2,4-dioxo-4-phenylbutyrate. The results are reported in Table 5.

TABLE 5

| Example No. | Modifier | Solvent | ee (%) | Conversion (%) |
|---|---|---|---|---|
| B49 | MeO-Cn | AcOH | 62 | 100 |
| B50 | MeO-Qd | AcOH | 61 | 100 |
| B51 | iso-Cn | AcOH | 62 | 97 |
| B52 | iso-Qd | AcOH | 61 | 100 |
| B53 | EXN-1 | AcOH | 74 | 100 |
| B54 | rubanol | AcOH | 61 | 100 |
| Comparative | HCn | AcOH | 64 | 100 |
| B55 | MeO-Cn | toluene | 18 | 100 |
| B56 | MeO-Qd | toluene | 4 | 100 |
| B57 | iso-Cn | toluene | 71 | 99 |
| B58 | iso-Qd | toluene | 4 | 10 |
| B59 | EXN-1 | toluene | 53 | 100 |
| B60 | rubanol | toluene | 62 | 100 |
| Comparative | HCn | toluene | 64 | 100 |

EXAMPLES B61–B71

Hydrogenation of Ethyl 4-phenyl-2-oxobutyrate

The procedure of Example B1 is followed using ethyl 4-phenyl-2-oxobutyrate. The results are reported in Table 6.

TABLE 6

| Example No. | Modifier | Solvent | ee (%) | Conversion (%) |
|---|---|---|---|---|
| B61 | MeO-Cn | AcOH | 81 | 100 |
| B62 | MeO-Qd | AcOH | 82 | 100 |
| B63 | iso-Cn | AcOH | 81 | 100 |
| B64 | iso-Qd | AcOH | 76 | 100 |
| B65 | EXN-1 | AcOH | 86 | 100 |
| B66 | rubanol | AcOH | 78 | 100 |
| Comparative | HCn | AcOH | 78 | 100 |
| B67 | MeO-Cn | toluene | 16 | 100 |
| B68 | MeO-Qd | toluene | racemic | 100 |
| B68 | iso-Cn | toluene | 66 | 100 |
| B69 | iso-Qd | toluene | 55 | 100 |
| B70 | EXN-1 | toluene | 46 | 100 |
| B71 | rubanol | toluene | 64 | 100 |
| Comparative | HCn | toluene | 57 | >95 |

EXAMPLE B72 AND COMPARATIVE EXAMPLE

Hydrogenation of Ethyl Pyruvate 5 mg of modifier are initially charged in a 50 ml pressure autoclave equipped with a magnetic stirrer and baffle. 50 mg of catalyst (JMC 94, batch 14017/01, pretreated under hydrogen at 400° C. for 2 h) are slurried in 2 ml of acetic acid and transferred to the autoclave. The substrate is dissolved in the rest of the solvent (total 20 ml) and likewise transferred to the autoclave. The autoclave is purged three times with argon and three times with hydrogen and then 60 bar of hydrogen are injected in. The reaction is started by switching on the magnetic stirrer. The temperature is kept constant at 25° C. with the aid of a cryostat. The pressure in the autoclave is kept constant during the reaction using a dome pressure regulator, and the hydrogen takeup in the reactor is measured by the pressure decrease in a reservoir.

After the end of the reaction, the reactor is decompressed, and the autoclave is purged three times with argon and then opened. The catalyst is filtered off. The conversion is determined by gas chromatography. The results are reported in Table 7. HCn means 10,11-dihydrocinchonine.

TABLE 7

| Example | Modifier | Time (min) | Conversion (%) | ee (%) | mmol of $H_2$/ g of catalyst |
| --- | --- | --- | --- | --- | --- |
| Comparative | HCn | 19 | 100 | 89 | 148 |
| B72 | A3 | 16 | 100 | 91 | 182 |

EXAMPLE B73 AND COMPARATIVE EXAMPLE

Hydrogenation of Methylglyoxal 1,1-dimethyl Acetal

The procedure is the same as in Example B72. The conversion is determined by gas chromatography. The results are reported in Table 8. HCn means 10,11-dihydrocinchonine.

TABLE 8

| Example | Modifier | Time (min) | Conversion (%) | ee (%) | mmol of $H_2$/ g of catalyst |
| --- | --- | --- | --- | --- | --- |
| Comparative | HCn | 120 | 51 | 71 | 24 |
| B73 | A3 | 120 | 61 | 79 | 35 |

EXAMPLES B74–B75 AND COMPARATIVE EXAMPLE

Hydrogenation of Ethyl 4-phenyl-2,4-dioxobutyrate

The procedure is the same as in Example B72. The conversion is determined by gas chromatography. The results are reported in Table 9. HCn means 10,11-dihydrocinchonine

TABLE 9

| Example | Amount of catalyst | Modifier (amount in | Time (min) | Conversion (%) | ee (%) | mmol/ g*min |
| --- | --- | --- | --- | --- | --- | --- |
| Comparative | 10 mg | HCn (2) | 95 | 95 | 56 | — |
| B74 | 125 mg | A3 (13) | 60 | 94 | 78 | 6.72 |
| B75 | 84 g | A3 (8400) | 90 | 99 | 79 | 2.7 |

What is claimed is:

1. A process for enantioselectively hydrogenating a prochiral ketone to an (S)-alcohol, which comprises hydrogenating the prochiral ketone in the presence of a platinum catalyst, a modifier and hydrogen, wherein the modifier is a compound of the formula XI with 8(R),9(S)-configuration

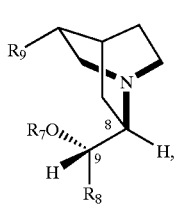

where
$R_9$ is H or $CH_3$—CH= and $R_7$ is H or methyl, and
$R_8$ is $C_6$–$C_{14}$-aryl which is unsubstituted or substituted by $C_1$–$C_4$-alkyl or $C_1$–$C_4$-alkoxy, or
$R_8$ is $C_5$–$C_{13}$-heteroaryl having a heteroatom selected from the group consisting of —N=, —O—, —S— and —N($C_1$–$C_4$-alkyl)- which heteroaryl is unsubstituted or substituted by hydroxy, $C_1$–$C_4$-alkyl or $C_1$–$C_4$-alkoxy.

2. A process according to claim 1, wherein the prochiral α-ketones are saturated or unsaturated, open-chain or cyclic compounds which contain 5 to 30 carbon atoms which are unsubstituted or substituted by radicals which are stable under the hydrogenation conditions, and the carbon chain is uninterrupted or interrupted by heteroatoms from the group of —O—, =N— and —NR'— where R' is H, $C_1$–$C_8$-alkyl, $C_5$–$C_8$-cycloalkyl, $C_6$–$C_{10}$-aryl or $C_7$–$C_{12}$-aralkyl.

3. A process according to claim 2, wherein the prochiral ketone is selected from the group consisting of α-ketocarboxylic acids, α-ketocarboxylic esters, α-ketoethers, α-ketoacetals and α,β-diketones.

4. A process according to claim 3, wherein the prochiral ketone corresponds to the formula, I, II, III, IV or V

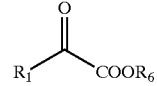

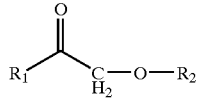

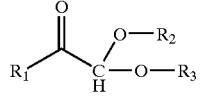

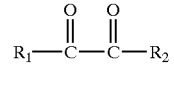

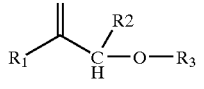

where
$R_1$, $R_2$, $R_3$ and $R_6$ are each independently a monovalent, saturated or unsaturated aliphatic radical having 1 to 12 carbon atoms, a saturated or unsaturated cycloaliphatic radical having 3 to 8 carbon atoms, a saturated or unsaturated heterocycloaliphatic radical having 3 to 8 ring members and one or two heteroatoms from the group of O, N and NR', a saturated or unsaturated cycloaliphatic-aliphatic radical having 4 to 12 carbon atoms, a saturated or unsaturated heterocycloaliphatic-aliphatic radical having 3 to 12 carbon atoms and one or two heteroatoms from the group of O, N and NR', an aromatic radical having 6 to 10 carbon atoms, a heteroaromatic radical having 4 to 9 carbon atoms and one or two heteroatoms from the group of O and N, an aromatic-aliphatic radical having 7 to 12 carbon atoms or a heteroaromatic-aliphatic radical having 5 to 11 carbon atoms and one or two heteroatoms from the group of O and N where R' is H, $C_1$–$C_8$-alkyl, $C_5$- or $C_6$-cycloalkyl, $C_6$–$C_{10}$-aryl, or $C_7$–$C_{12}$-aryl, or $R_1$ and $R_2$ or $R_1$ and $R_6$ together are $C_1$–$C_6$-alkylene or $C_3$–$C_8$-1,2-cycloalkylene, or $C_2$–$C_4$-alkylene or $C_3$–$C_8$-cycloalkylene fused to 1,2-phenylene, and $R_3$ is as defined above, $R_2$ and $R_3$ together are $C_1$–$C_6$-alkylene, $C_1$–$C_8$-alkylidene, $C_3$–$C_8$-1,2-cycloalkylene, $C_3$–$C_8$-cycloalkylidene, benzylidene, 1,2-phenylene, 1,2-pyridinylene, 1,2-naphthylene, or $C_3$–$C_4$-alkylene or $C_3$–$C_8$-1,2-cycloalkylene fused to 1,2-cycloalkylene or 1,2-phenylene, and $R_1$ is as defined above, and $R_1$, $R_2$, $R_3$ and $R_6$ are each unsubstituted or substituted by one or more, identical or different radicals selected from the group of $C_1$–$C_4$-alkyl, $C_2$–$C_4$-alkenyl, $C_1$–$C_4$-alkoxy, $C_1$–$C_4$-haloalkyl, $C_1$–$C_4$-hydroxyalkyl, $C_1$–$C_4$-alkoxymethyl or -ethyl, $C_1$–$C_4$-haloalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —$OR_4$, —$OC(O)R_4$, —$NH_2$, —$NHR_4$, —$NR_4R_5$, —NH—C(O)—$R_4$, —$NR_4$—C(O)—$R_4$, —$CO_2R_4$, —$CO_2$—$NH_2$, —$CO_2$—$NHR_4$, —$CO_2$—$NR_4R_5$ where $R_4$ and $R_5$ are each independently $C_1$–$C_4$-alkyl, cyclohexyl, cyclohexylmethyl, phenyl or benzyl.

5. A process according to claim 1, wherein $R_8$, as aryl and heteroaryl, is a monocyclic or fused polycyclic radical.

6. A process according to claim 5, wherein the aryl and heteroaryl comprise rings having 5 or 6 ring members.

7. A process according to claim 1, wherein the modifier is a compound of the formula XIa with 8(R),9(S)-configuration

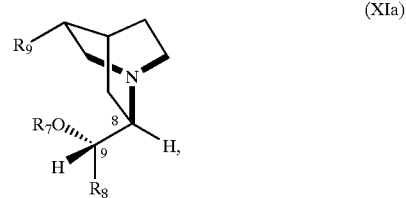

(XIa)

where
$R_9$ is H or $CH_3$—CH= and $R_7$ is H or methyl,
$R_8$ is a radical of the formula

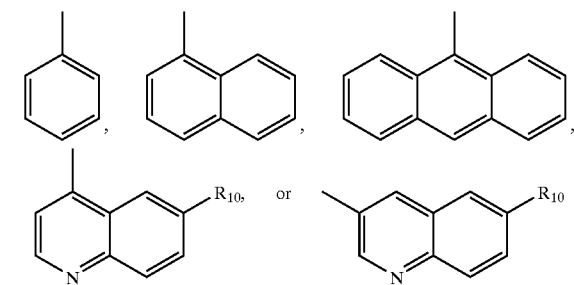

and $R_{10}$ is H, OH or $C_1$–$C_4$-alkoxy.

8. A process according to claim 1, wherein the platinum metal is used in an amount of 0.01 to 10% by weight, based on the prochiral ketone used.

9. A process according to claim 1, wherein the modifier is used in an amount of 0.1 to 10 000% by weight, based on the platinum metal used.

10. A process according to claim 1, wherein the hydrogenation is carried out under a hydrogen pressure of up to 200 bar.

11. A process according to claim 1, wherein the hydrogenation is carried out at a reaction temperature of –50 to 100° C.

12. A process according to claim 4, wherein R' is $C_1$–$C_4$-alkyl.

13. A process according to claim 4, wherein R' is phenyl or naphthyl.

14. A process according to claim 4, wherein R' is phenylmethyl or phenylethyl.

* * * * *